(12) United States Patent
Hazebrouck et al.

(10) Patent No.: US 7,198,642 B2
(45) Date of Patent: Apr. 3, 2007

(54) ORTHOPAEDIC SPACER

(75) Inventors: Stephen A. Hazebrouck, Winona Lake, IN (US); Scott C. Brown, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 10/952,581

(22) Filed: Sep. 24, 2004

(65) Prior Publication Data

US 2005/0107794 A1    May 19, 2005

Related U.S. Application Data

(63) Continuation-in-part of application No. 10/403,612, filed on Mar. 31, 2003.

(51) Int. Cl.
A61F 2/28 (2006.01)
A61F 2/46 (2006.01)
A61B 17/56 (2006.01)

(52) U.S. Cl. .................. 623/16.11; 623/23.44; 623/23.47; 606/62

(58) Field of Classification Search ............. 623/16.11, 623/23.44, 23.47; 606/62, 63, 64
See application file for complete search history.

(56) References Cited

U.S. PATENT DOCUMENTS

| | | | |
|---|---|---|---|
| 2,779,966 A | 2/1957 | Torchia | |
| 3,801,213 A | 4/1974 | Eversole | |
| 4,011,602 A | 3/1977 | Rybicki | |
| 4,016,874 A | 4/1977 | Maffei et al. | |
| 4,384,373 A | 5/1983 | Sivash | |
| 4,467,794 A * | 8/1984 | Maffei et al. | ............... 606/62 |
| 4,502,160 A | 3/1985 | Moore et al. | |
| 4,634,444 A | 1/1987 | Noiles | |
| 4,655,462 A | 4/1987 | Balsells | |
| 4,676,797 A | 6/1987 | Anapliotis et al. | |
| 4,787,907 A | 11/1988 | Carnignan | |
| 4,826,144 A | 5/1989 | Balsells | |

(Continued)

FOREIGN PATENT DOCUMENTS

DE    3535158 A    4/1987

(Continued)

OTHER PUBLICATIONS

Extended European Search Report dated Dec. 21, 2005, for corresponding EP application 05255808.7.

(Continued)

*Primary Examiner*—Corrine McDermott
*Assistant Examiner*—Thomas J Sweet

(57) ABSTRACT

Two spacer components and a retaining ring are part of an orthopaedic system. The system may also include trial or implant stem components that are inserted or implanted in the proximal and distal ends of the long bone. One spacer segment has a male portion and the other spacer segment has a transverse female slot. The male portion and female slot are positioned to allow the male portion to be moved into and out of the female slot in a direction other than the proximal-distal direction. The retaining ring is then threaded into a locked position to limit relative movement between the male portion and female slot. The spacer segments can thus be connected after the segments have been connected to the native bone without damaging the soft tissue at the native bone through distraction.

18 Claims, 13 Drawing Sheets

U.S. PATENT DOCUMENTS

| | | | |
|---|---|---|---|
| 4,830,344 A | | 5/1989 | Balsells |
| 4,876,781 A | | 10/1989 | Balsells |
| 4,888,021 A | | 12/1989 | Forte |
| 4,915,366 A | | 4/1990 | Balsells |
| 4,934,666 A | | 6/1990 | Balsells |
| 4,938,768 A | * | 7/1990 | Wu .......................... 623/23.47 |
| 5,011,496 A | | 4/1991 | Forte |
| 5,072,070 A | | 12/1991 | Balsells |
| 5,079,388 A | | 1/1992 | Balsells |
| 5,082,390 A | | 1/1992 | Balsells |
| 5,100,407 A | | 3/1992 | Conrad |
| 5,108,078 A | | 4/1992 | Balsells |
| 5,108,437 A | | 4/1992 | Kenna |
| 5,117,066 A | | 5/1992 | Balsells |
| 5,139,276 A | | 8/1992 | Balsells |
| 5,314,479 A | | 5/1994 | Rockwood, Jr. et al. |
| 5,334,184 A | | 8/1994 | Bimman |
| 5,352,227 A | | 10/1994 | O'Hara |
| 5,358,524 A | * | 10/1994 | Richelsoph .............. 623/23.47 |
| 5,411,348 A | | 5/1995 | Balsells |
| 5,601,567 A | * | 2/1997 | Swajger et al. ............. 606/102 |
| 6,197,065 B1 | | 3/2001 | Martin et al. |
| 6,290,725 B1 | | 9/2001 | Weiss |
| 6,357,194 B1 | | 3/2002 | Jones, Jr. |
| 6,364,909 B1 | | 4/2002 | McGee |
| 6,443,954 B1 | * | 9/2002 | Bramlet et al. ............... 606/62 |
| 6,447,549 B1 | | 9/2002 | Taft |
| 6,454,810 B1 | * | 9/2002 | Lob ........................ 623/23.47 |
| 6,613,092 B1 | | 9/2003 | Kana et al. |
| 6,648,889 B2 | * | 11/2003 | Bramlet et al. ............... 606/62 |
| 6,712,855 B2 | | 3/2004 | Martin et al. |
| 6,712,858 B1 | | 3/2004 | Grundel et al. |
| 6,790,234 B1 | * | 9/2004 | Frankle ................... 623/19.12 |
| 2003/0149486 A1 | * | 8/2003 | Huebner .................. 623/19.11 |
| 2003/0204262 A1 | | 10/2003 | Ferguson et al. |
| 2003/0204267 A1 | | 10/2003 | Hazebrouck et al. |
| 2004/0193266 A1 | * | 9/2004 | Meyer ..................... 623/16.11 |
| 2004/0193267 A1 | | 9/2004 | Jones et al. |
| 2004/0193268 A1 | | 9/2004 | Hazebrouck et al. |
| 2004/0236339 A1 | * | 11/2004 | Pepper ........................ 606/80 |
| 2005/0107883 A1 | | 5/2005 | Goodfried et al. |

FOREIGN PATENT DOCUMENTS

| | | |
|---|---|---|
| DE | 19633865 A | 2/1998 |
| DE | 3903438 A | 7/1998 |
| DE | 19722389 A | 7/1999 |
| EP | 0212192 A1 | 3/1987 |
| EP | 0 359 485 A1 | 3/1990 |
| EP | 1234557 A | 2/2002 |
| EP | 1358860 A | 4/2002 |
| FR | 2633509 A | 7/1988 |
| WO | WO 02/05732 A | 1/2002 |

OTHER PUBLICATIONS

U.S. Appl. Ser. No. 2001/041941, filed Nov. 15, 2001, Boyer, II et al.

Centerpulse Orthopedics, Inc. web site announcement: Centerpulse Orthopedics Announces Launch of Implant System for Revision and Trauma Patients; http://www.centerpulseorthopedics.com/us/products/news/most_options_launch_12_09. (4 pages); Dec. 9, 2002.

Centerpulse Orthopedics, Inc. web site page: MOST Options™; Modular Knee and Hip Otpions for Severe Bone Loss and Trauma; http://www.centerpulseorthopedics.com/most_options/knee/index. (2 pages).

Wright Medical Technology, Inc.: Guardian™ Limb Salvage System: Surgical Technique brochure: *Total Femoral Replacement.* 2001, Wright Medical Technology, Inc. (19 pages).

Wright Medical Technology, Inc.,: Guardian™ Limb Salvage System: Surgical Technique brochure: *Distal Femoral Replacement* 2001, Wright Medical Technology, Inc. (19 pages).

Wright Medical Technology, Inc., Guardian™ Limb Salvage System: Surgical Technique brochure: *Proximal Femoral Replacement.* 2001, Wright Medical Technology, Inc. (11 pages).

Biomet®, Inc. website: Finn® Salvage/oncology System; http://www.biomet.com/knees/finn.cfm 2001, 2002. (Form No. Y-BMT-698/123100M) (2 pages).

Howmedica Osteonics Corp. web site: Product Overview: Modular-Replacement System: http://www.howost.com/kneesystems/mrs/text.php; http://www.howost.com/kneesystems/mrs/overview.htm; http://www.howost.com/kneesystems/mrs/proxfemur.htm; http://www.howost.com/kneesystems/mrs/distalfemur.htm; http://www.howost.com/kneesystems/mrs/totalfemurr.htm; http://www.howost.com/kneesystems/mrs/proxtibiar.htm; http://www.howost.com/kneesystems/mrs/shoulderrhtm. 1997, Howmedica Osteonics Corp. (7pages).

Biomet®, Inc. *Knee System Modularity and Surgical Latitude* brochure. 1995. (Form No. Y-BMT-382/021095/H) (22 pages).

Biomet®, Inc. *Proxmial Humeral Replacement™ System* brochure 1996. (Form No. Y-BMT-466/043096/H) (2 pages).

Biomet®, Inc. *Finn™ Knee System Product Release Overview* brochure, including pp. 1-30.

Biomet®, Inc. *The Finn Knee: Rotating Hinge Replacement of the Knee Preliminary Report of New Design* document, pp. 413-416.

Howmedica Osteonics Corp. Modular Replacement System: *A Simple, Comprehensive, Modular System for Radical Bone Resections of Proximal Femur, Distal Femur, Total Femur, Proximal Tibia, Proximal Humerus* brochure. 1997 Howmedica, inc. (7100-0-001-0 5M Sep. 1997, 5807 TG/HAR). (6 pages).

Stryker Howmedica Osteonics Corp: *Modular Rotating Hinge Knee System* brochure. 2000 Stryker COrporation (6481-2-085 LI 06/00). (4 pages).

Howmedica International: *Howmedica Modular Resection System* brochure (XXK/01/0391/4E). (12 pages).

Sulzer Medica: *Sulzer™ Orthopedics MOST™ System* brochure (1000-01-607) (Oct. 1997, 1.5M 1997 Sulzer Orthopedics, Inc. (2 pages).

Wright Medical Technology, inc.: Segmental Oncology System - *The S.O.S. Proximal Femur* brochure (4 pages).

Wright Medical Technology, Inc.: Segmental Orthopedic System - *The Salvage Solution - The S.O.S. Proximal Femur* brochure (7pages).

Balseal Engineering, Canted Coil Springs web page: Aug. 21, 2002.

Stryker Howmedica Osteonics: *Modular Replacement System: Distal Femoral Resection for Large Segmental Replacements - Surgical Technique Brochure.*

* cited by examiner

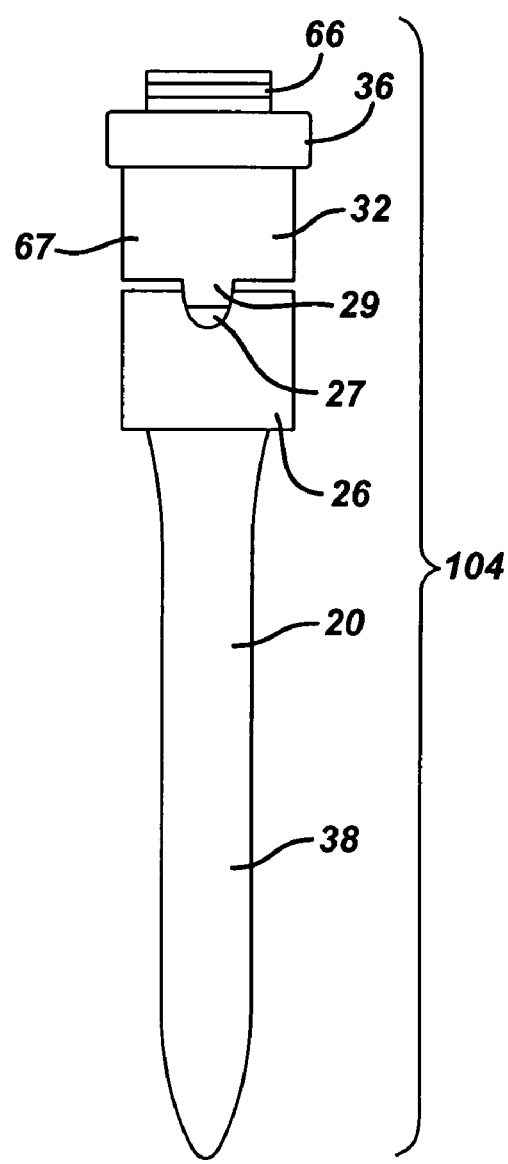
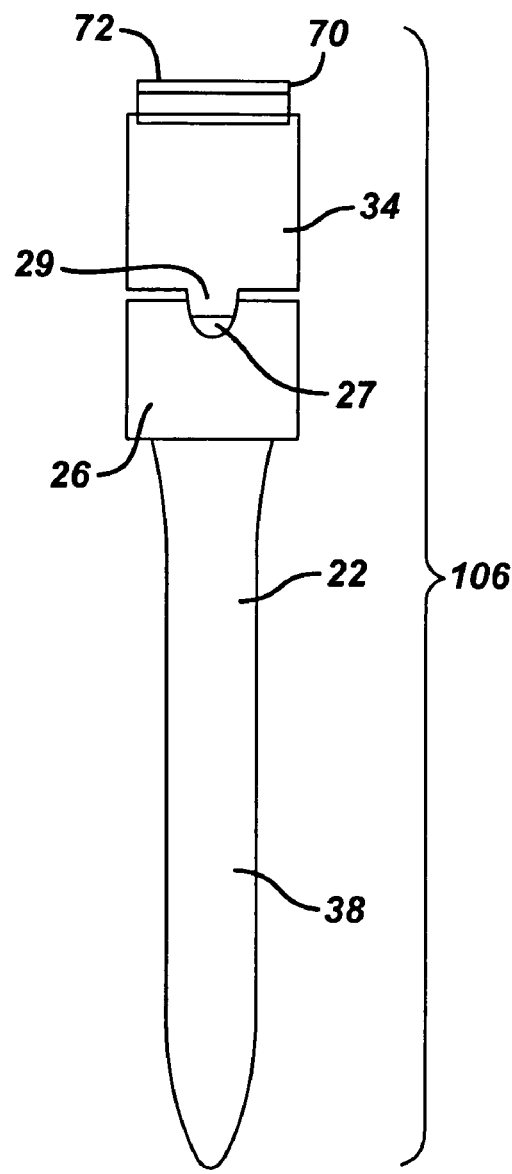

ORTHOPAEDIC SPACER

CROSS-REFERENCE TO RELATED APPLICATIONS

The present application is a continuation-in-part of U.S. patent application Ser. No. 10/403,612, entitled "Dovetailed Intercalary Segmental Implant" filed on Mar. 31, 2003, by Stephen A. Hazebrouck, which is incorporated by reference herein in its entirety.

FIELD OF THE INVENTION

The present invention relates to prosthetic systems for replacement of parts of bones, and more particularly to prosthetic systems having components that can be connected and disconnected in situ without damaging soft tissue through distraction of bone segments.

BACKGROUND OF THE INVENTION

Severe trauma and disease can lead to significant amounts of bone loss. In some instances, it is necessary to excise intercalary bone from a long bone, that is, part of the diaphysis or bone shaft between the ends of the long bone, but it is not necessary to excise the ends of the long bone. Thus, for example, a portion of the shaft of the femur may need to be excised to remove a malignancy, while the ends of the femur defining parts of the hip and knee joint may be healthy. Similarly, it may be necessary to excise part of the shaft of the tibia or humerus while the ends of these bones are healthy. Rather than remove the healthy ends of the bone, it may be desirable to leave the healthy portions of the bone in place and remove the damaged or diseased bone. In these circumstances, the empty span between the ends of the bone must be replaced with some type of mid-shaft prosthesis that spans the distance between the native bone ends. The mid-shaft prosthesis can include stems that fit into the intramedullary canals of the native bone ends and a body that extends between these stems. However, it may be difficult to implant such a mid-shaft prosthesis. Implantation can require that the native bone ends be distracted proximally and distally in order to fit the mid-shaft prosthesis into position. Since the native bone ends are surrounded by and connected to soft tissue, distraction of the native bone ends can damage the soft tissue and the connections between the soft tissue and the native bone ends.

During surgical procedures to replace part of a bone with a prosthesis, orthopaedic trials are typically used. A surgeon uses an orthopaedic trial to ensure that the proper implant size will be used, to make the appropriate cuts and reams in the bone, and to ensure a proper alignment and component thickness prior to implanting the prosthetic components.

For orthopaedic trials to be most useful, it is desirable that they replicate the sizes and shapes of the final implant components to be used. Therefore, it is desirable that orthopaedic trials offer the same flexibility as offered by the final implants. To optimize the utility of such orthopaedic trials, it is also desirable that these orthopaedic trials also be easily and quickly assembled or connected and disassembled or disconnected.

For orthopaedic trials that are sized and shaped to mimic final intercalary implant components, the mid-shaft trials can include stems that fit into the intramedullary canals of the native bone ends and a trial body that extends between these stems. However, as described above with respect to intercalary implants, it may be difficult to insert such a mid-shaft trial without damaging the soft tissue at the native bone ends.

SUMMARY OF THE INVENTION

The present invention addresses the need for orthopaedic components, such as trials and implants, that offer flexibility, that can be easily and quickly assembled or connected and disassembled or disconnected, and that can be temporarily inserted or implanted while minimizing damage to the soft tissue at the remaining portions of native bone.

In one aspect the present invention addresses these needs by providing an orthopaedic system comprising a set of implant components sized and shaped to replace a portion of a bone, a set of trial components sized and shaped to replicate or duplicate at least one feature of the implant components and a set of instruments for use in preparing the bone to receive the implant components. At least one of the sets includes a first member having a longitudinal axis, a second member having a longitudinal axis, and a retainer. One of the members has a male portion and the other of the members has wall sections defining a female portion. The female portion is capable of receiving the male portion to connect the first and second members together. The female portion and the male portion are sized and shaped so that the male portion can be moved into the female portion through relative movement in a direction other than longitudinal. The retainer is movable between an unlocked position wherein relative movement between the male portion and female portion is possible and a locked position wherein relative movement between the male portion and female portion is restricted.

In another aspect, the present invention addresses these needs by providing an intercalary orthopaedic system to span a space in the shaft of a long bone between native proximal and distal ends of the long bone. The system comprises a first spacer segment, a second spacer segment and a retaining ring. The first spacer segment is to be secured to the native proximal end of the long bone and has a longitudinal axis. The second spacer segment is to be secured to the native distal end of the long bone and has a longitudinal axis. One of the spacer segments has a male portion and the other of the spacer segments has surfaces defining a female portion. The female portion is capable of receiving the male portion to connect the first and second spacer segments together to span the space in the shaft of the long bone. The male and female portions may comprise a T-shaped projection and a mating T-slot, mating dovetails, or tongues and grooves, for example. The female portion has a threaded exterior surface. The female portion and the male portion are sized and shaped so that the male portion can be moved into the female portion through relative movement in a direction other than longitudinal. The retaining ring has a threaded interior surface sized and shaped to be capable of being threaded onto the threaded exterior surface of the female portion to retain the first and second spacer segments together when the male portion is received in the female portion.

In another aspect, the present invention provides an intercalary orthopaedic system spanning a space in the shaft of a long bone between native proximal and distal ends of the long bone comprising a first spacer segment, a segment spacer segment and a retaining ring. The first spacer segment is secured to the native proximal end of the long bone. The second spacer segment is secured to the native distal end of the long bone. One of the spacer segments has a male portion and the other of the spacer segments has surfaces defining a female portion. The female portion receives the male portion to connect the first and second spacer segments together to span the space in the shaft of the long bone. The female portion has a threaded exterior surface. The retaining ring has a threaded interior surface threaded onto the threaded exterior surface of the female portion to retain the first and second spacer segments together.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 22 is an elevation or side view of a first sub-assembly of a first spacer segment, first stem component and retaining ring;

FIG. 23 is an elevation or side view of a second sub-assembly of a second spacer segment and a second stem component;

DETAILED DESCRIPTION

Figure 1:
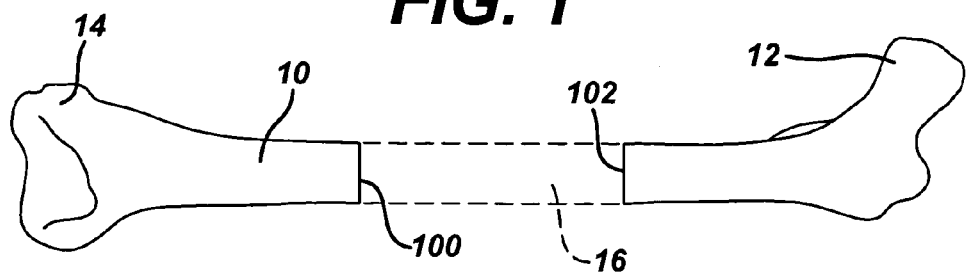
FIG. 1 is a top plan or anterior view of a femur, showing the native proximal and distal ends of the femur and showing an excised intercalary segment of the diaphysis of the femur in phantom between the native ends of the femur.

FIG. 1 illustrates a long bone, and in particular, a femur 10 with proximal and distal ends 12, 14. The proximal end 12 of the femur 10 comprises the femoral head and adjacent bone tissue; the distal end 14 of the femur comprises the femoral condyles and adjacent bone tissue. FIG. 1 also illustrates in phantom the intercalary segment 16 of diaphyseal bone that has been removed, due to, for example, disease or severe trauma. Although the present invention is illustrated in use with the femur, it should be understood that the invention is not so limited; the invention could be used in any other long bone, such as the tibia or humerus, where a portion of the shaft has been removed or is missing.

Figure 2:
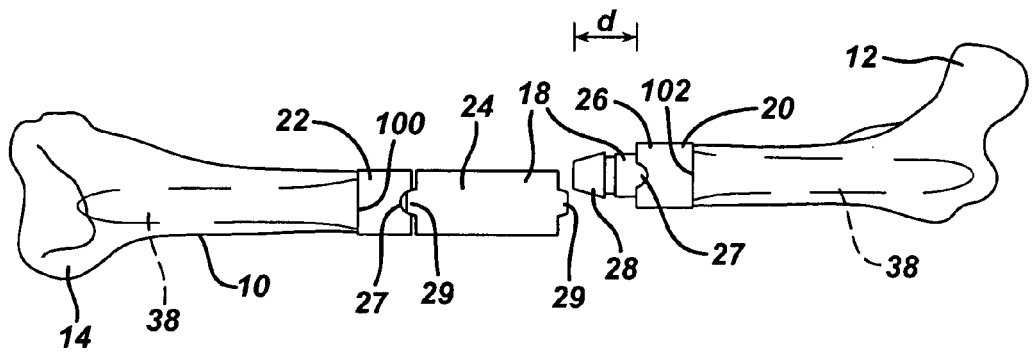
FIG. 2 is a top plan or anterior view of the femur of FIG. 1, shown with one type of intercalary prosthesis trial prior to connection of all the parts of the intercalary prosthetic trial.
Figure 3:
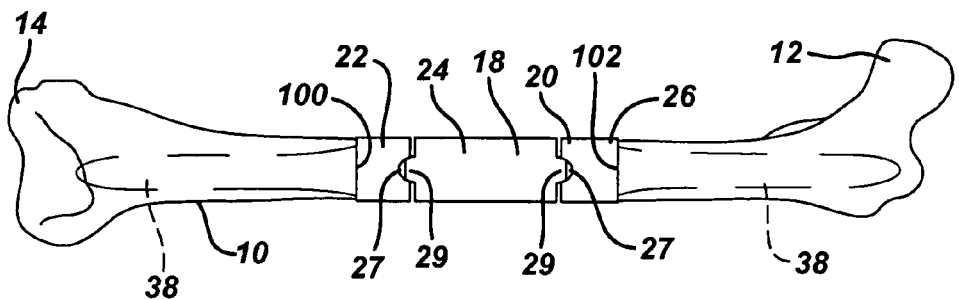
FIG. 3 is a top plan or anterior view of the femur of FIGS. 1–2, shown with all parts of the intercalary prosthesis trial connected together.

FIG. 2 illustrates the femur 10 of FIG. 1 in an intra-operative state, with a modular mid-shaft prosthetic trial system 18, prior to connection of the trial components. FIG. 3 illustrates the femur and trial system 18 of FIGS. 1–2 after the trial components have been connected. The mid-shaft prosthetic trial system 18 of FIGS. 2–3 is that disclosed in U.S. patent application Ser. No. 10/135,610 filed on Apr. 30, 2002 and entitled "Quick Disconnect Orthopaedic Trials" (Publication No. 20030204262A1). That patent application is incorporated by reference herein in its entirety.

The mid-shaft prosthetic trial system 18 illustrated in FIGS. 2–3 comprises a proximal stem trial 20, a distal stem trial 22 and a spacer trial 24. Each of the stem trials 20, 22 includes a head portion 26 from which extends a male connection post 28. The head portion 26 also includes a pair of notches 27 that receive tabs 29 on the spacer trial 24. Each of the stem trials 20, 22 also includes a stem portion 30 that is shaped to be received in the intramedullary canal of the bone.

As shown in FIG. 2, to temporarily insert the mid-shaft prosthetic trial system 18 in the bone 10, the two stem trials 20, 22 may be inserted in the intramedullary canals of the two spaced ends 12, 14 of the bone 10. The spacer trial 24 can be connected to one of the stem trials 20, 22 before the stem portion is inserted, or could also be connected after the stem portion is inserted. To complete the assembly, the native proximal and distal ends 12, 14 of the bone 10 with the proximal and distal stem trials 20, 22 and spacer trial 24 must be distracted, or moved in the proximal-distal direction, by at least a distance "d" (shown in FIG. 2), corresponding with the length of the post 28 so that the post 28 can be inserted into the mating female portion of the spacer trial 24. In the illustrated embodiment, the dimension "d" is typically on the order of 20 mm. This degree of proximal-distal distraction of the native bone ends 12, 14 could damage the surrounding soft tissue and soft tissue that is connected to the native bone ends 12, 14.

To avert the potential for soft tissue damage, the present invention obviates the need for proximal-distal distraction of the native bone ends 12, 14 during trialing while retaining the advantages of the system disclosed in U.S. patent application Ser. No. 10/135,610. As shown in FIGS. 4–6 and 17–20, two stem trial components 20, 22 of the type disclosed in U.S. patent application Ser. No. 10/135,610 (or permanent stem implant components of the type disclosed for example in application Ser. No. 10/135,791) can be connected to an intervening three-part spacer without undue distraction of the native proximal and distal end bone portions 12, 14. The three-part spacer of the present invention comprises a first spacer segment 32, a second spacer segment 34 and a retaining ring 36.

Figure 4:
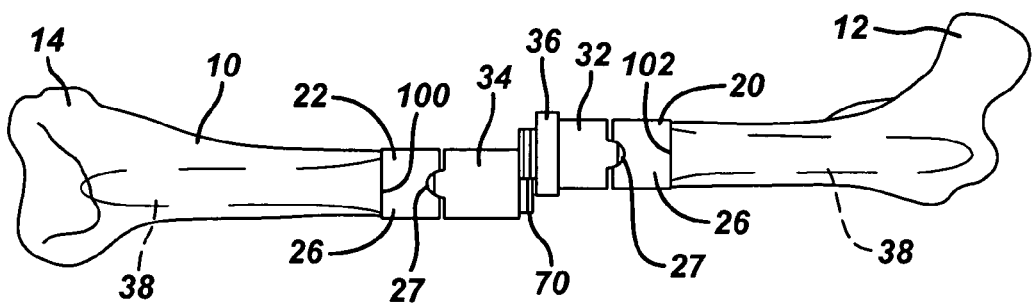
FIG. 4 is a top plan or anterior view of the femur of FIG. 1, shown with an embodiment of the intercalary prosthetic system of the present invention prior to connection of all the parts of the intercalary prosthetic system.
Figure 5:
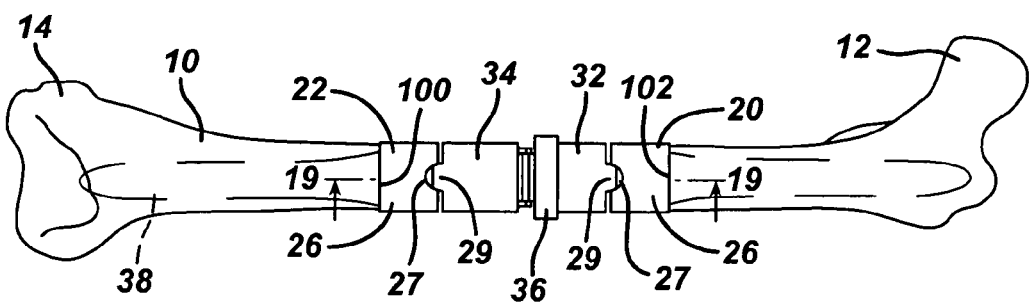
FIG. 5 is a top plan or anterior view of the femur of FIGS. 1 and 4, shown with parts of the intercalary prosthetic system of FIG. 4 connected together and prior to turning the retaining ring.
Figure 6:
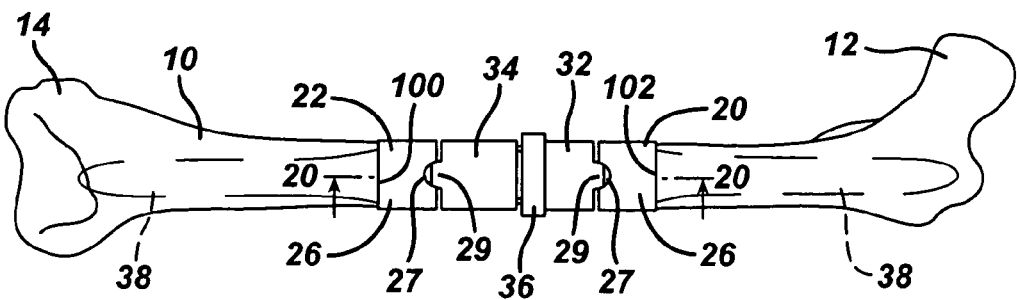
FIG. 6 is a top plan or anterior view of the femur of FIGS. 1 and 4–5, shown with parts of the intercalary prosthetic system connected together as in FIG. 5, and after turning the retaining ring to lock the first and second spacer segments together.
Figure 7:
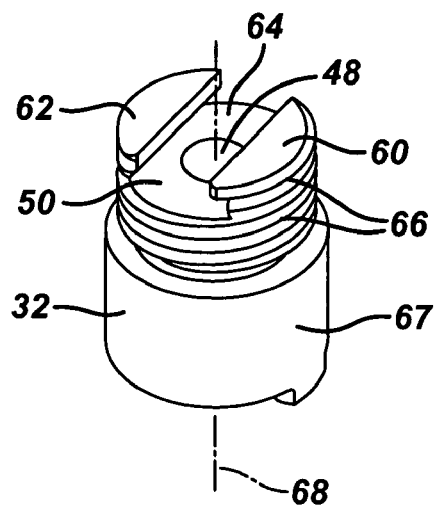
FIG. 7 is a perspective view of one embodiment of a first spacer segment for use with the intercalary prosthetic system of the present invention.
Figure 8:
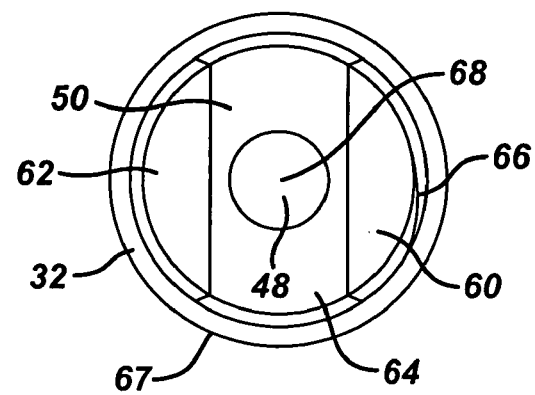
FIG. 8 is a top plan view of the spacer segment of FIG. 7.
Figure 9:
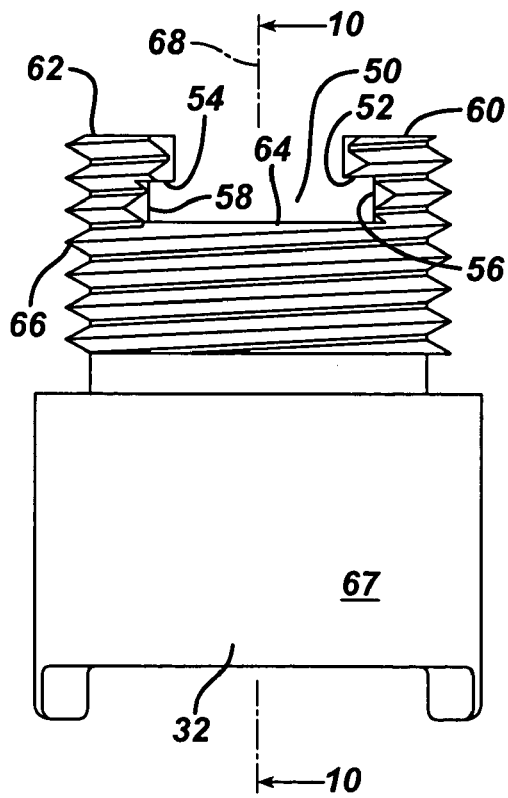
FIG. 9 is a side view or elevation of the spacer segment of FIGS. 7–8.

An intercalary orthopaedic system including the three-part spacer of the present invention could include stem components 20, 22 like those shown in FIGS. 4–6 with stems 38 of different lengths or other different characteristics. Generally, all of the stem components 20, 22 would have head portions 26 of the same size and shape to allow the stem components to be used interchangeably in the system described in U.S. patent application Ser. No. 10/135,610. Thus, the posts 28 would be the same dimensions and shapes so that they can be received in all of the female parts of the system.

The intercalary orthopaedic system would typically include surgical instruments for resecting and preparing the bone, intercalary implants and intercalary trials. The intercalary implants may have features such as those disclosed in the following U.S. patent application Ser. No. 10/403,612, entitled "Dovetailed Intercalary Segmental Implant" filed on Mar. 31, 2003, by Stephen A. Hazebrouck (incorporated by reference herein in its entirety); Ser. No. 10/403,357 entitled "Intercalary Segmental Implant," filed on Mar. 31, 2003 by Natalie Heck and Michael C. Jones (incorporated by reference herein in its entirety); and Ser. No. 10/135,791 entitled "Modular Limb Preservation System," filed on Apr. 30, 2002 by Stephen A. Hazebrouck, Nick A. Deeter, Mark E. Ruhling, Mark B. Lester, and Joe William Ferguson (incorporated by reference herein in its entirety).

It should be understood that the principles of the present invention could also be applicable to other intercalary systems and to other orthopaedic systems (such as systems for replacing portions of bone at a joint such as the knee or hip, for example). Accordingly, the present invention should not be limited to the features of any trial, implant, instrument, system or kit unless expressly called for in the claims.

As used herein, "trial" means a device that replicates one or more features of an implant component and that is intended to be temporarily placed in the patient's body to allow intraoperative assessment of the effects of using that implant component, and to be removed from the patient's body and replaced with an implant component during the same surgical procedure. Typically the trial replicates one or more dimensional features of the implant component to allow for assessment of the size of the implant component. In the case of orthopaedic systems, several trials are usually included in the system, corresponding with the sized of implants available in the system. Many orthopaedic trials come in contact with native bone, or a resected surface of native bone.

It should also be understood that references herein to the first spacer segment 32, second spacer segment 34, proximal stem component and distal stem component are intended to be generic terms including both trial spacer segments or stem components and implant spacer segments or stem components unless expressly limited to one or the other type of segment or component. For example, the expression "first spacer segment" includes both trial spacer segments and implant spacer segments unless expressly limited to one or the other type of spacer segment. Thus, although the system illustrated in FIGS. 4–25 has features that may be particularly applicable to orthopaedic trials, it should be understood that the principles of the present invention are applicable to implants as well. Moreover, the principles of the present invention could be applied to surgical instruments, and could also be applied to other medical and non-medical uses.

Figure 10:
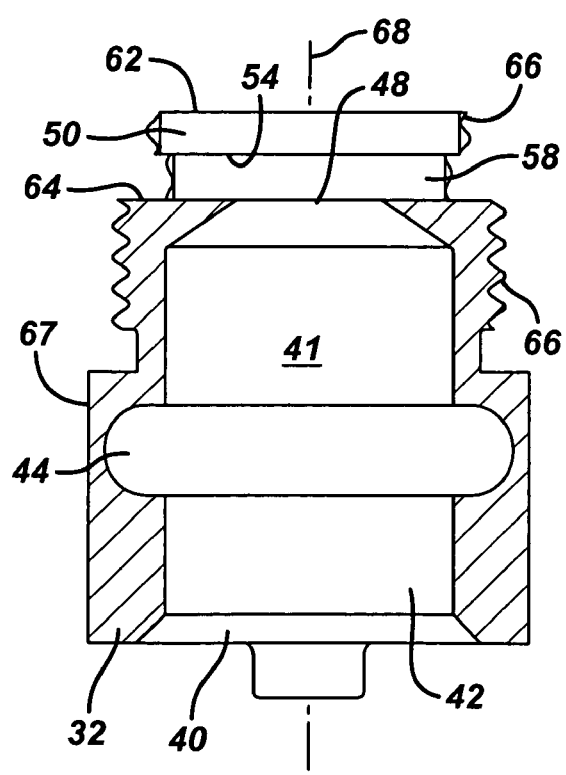
FIG. 10 is a cross-section of the spacer segment of FIGS. 7–9, taken along line 10—10 of FIG. 9.
Figure 13:
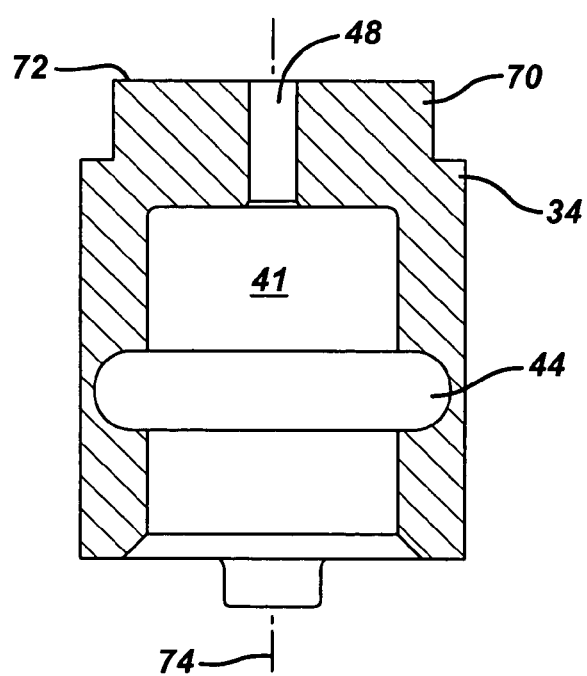
FIG. 13 is a cross-section of the spacer segment of FIGS. 11–12, taken along line 13—13 of FIG. 11.

Referring now to FIGS. 10 and 13, the illustrated first spacer segment 32 and second spacer segment 34 have open female ends 40 with chamfers leading to interior walls 41 defining interior bores 42. The interior wall 41 of each spacer segment 32, 34 also has a circular interior groove 44. In the illustrated embodiments, the interior grooves 44 are spaced 0.325 inches from the open female end 40; each illustrated groove 44 comprises a full radius of 0.200 inches.

Each bore 42 can receive the post 28 of one of the stem components 20, 22. The interior bores 42 and interior grooves 44 of both trial segments 32, 34 are similar to those described in U.S. patent application Ser. No. 10/135,610 so that each bore 42 can also receive and temporarily lock with a post 28 of one of male ends of one of the other trial system components described in U.S. patent application Ser. No. 10/135,610. The depth of the bore 42 of the first trial segment 32 is calibrated to the length of the posts so that any trial component of the system having a post like that described in U.S. patent application Ser. No. 10/135,610 can mate with the first trial segment 32. A garter-type canted-coil spring of the type illustrated in FIGS. 15–16 of U.S. patent application Ser. No. 10/135,610, available from Bal Seal Engineering Co., Inc. of Foothill Ranch, California (Part No. X205498), may be included within the interior groove 44 each of the illustrated trial segments 32,34 for temporarily locking the male posts 28 within the trial segments 32, 34. Such a garter-type canted-coil spring is shown at 46 in FIGS. 17–20.

It should be understood that the interiors of the first and second spacer segments 32, 34 may vary from those illustrated if the first and second spacer segments are intended to complement a components of a trial system having shapes and retention mechanisms different from those illustrated for the proximal and distal stem trials 20, 22. The present invention is not limited to any particular interior structure for the first and second spacer segments and is not limited to the use of canted-coil springs unless expressly called for in the claims. Moreover, if the segments are to be used as orthopaedic implants instead of trials, it is expected that some connection mechanism, such as Morse tapers, would be used instead of the canted-coil spring and groove system illustrated.

Both the first spacer segment 32 and the second spacer segment 34 have diametrically opposed tabs 29 like those described in U.S. patent application Ser. No. 10/135,791 and U.S. patent application Ser. No. 10/135,610. Each tab 29 can be received in one of the notches 27 of one of the stem components 20, 22. However, it should be understood that the invention is not limited to the use of such tabs and notches unless expressly called for in the claims. Other anti-rotation features can be used, or, it may not be necessary to include anti-rotation features in every case.

As shown in FIGS. 7–8, 10, 12–13 and 17–20, both the first spacer segment 32 and the second spacer segment 34 also have pressure relief bores 48 at the end walls defining the interior bores 42 so that air pressure can be relieved as stem components 20,22 and spacer segments 32, 34 are brought together. It should be understood that the locations, shapes and sizes shown for the pressure relief bores 48 are provided for purposes of illustration only; the invention is not limited to the illustrated means of relieving pressure unless expressly called for in the claims.

Figure 21:
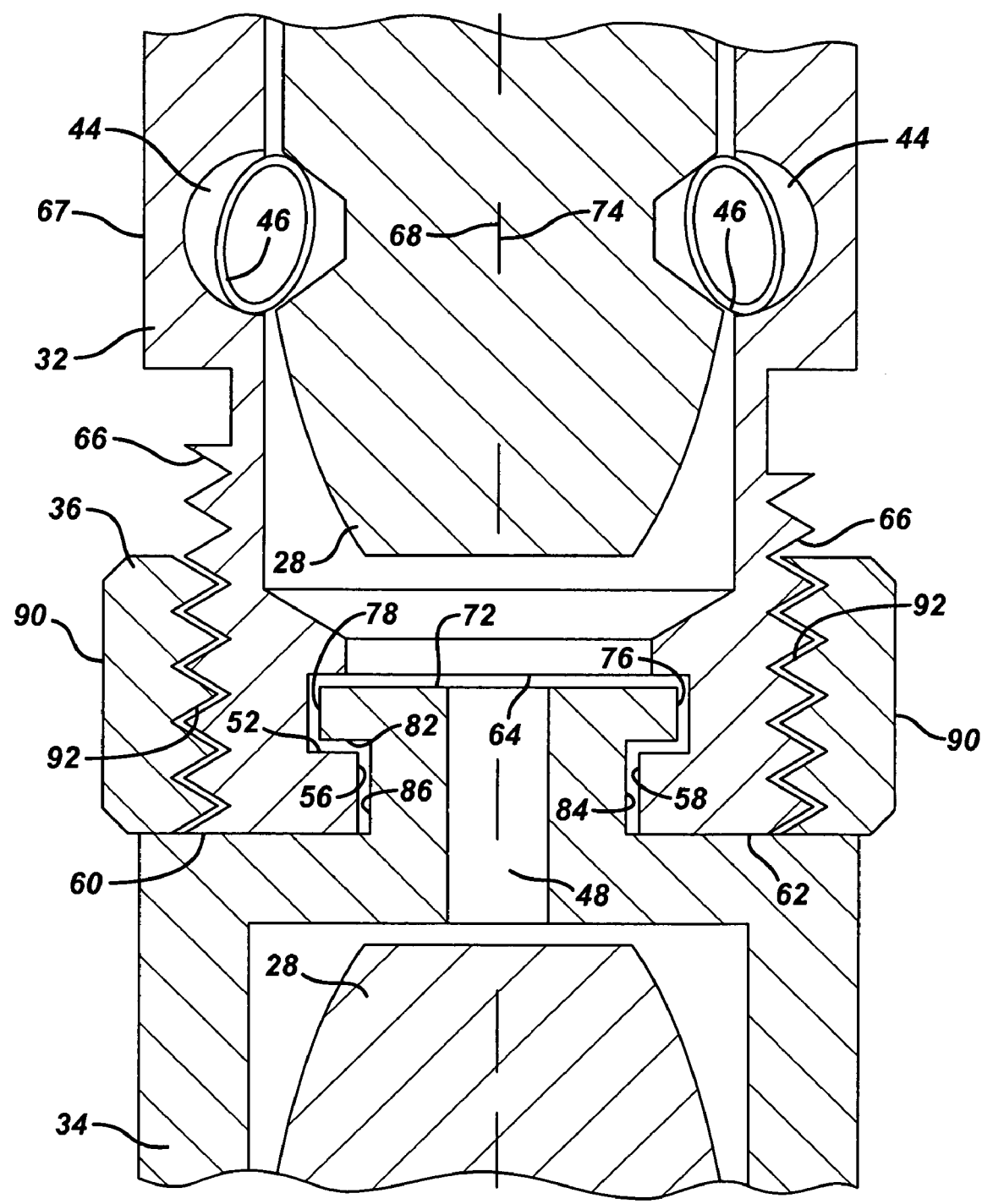
FIG. 21 is an enlarged cross-section of the connection between the first and second spacer segments with the retaining ring in the locked position.

Referring to FIGS. 7–10, the first spacer segment 32 includes exterior wall sections defining an exterior female portion 50 opposite the opening into the opening 40 into the interior bore 42. As best seen in FIG. 21, the exterior wall sections of the illustrated first spacer segment 32 include: a pair of spaced co-planar inner shoulders 52, 54; a pair of spaced parallel intermediate inner walls 56, 58; a pair of co-planar end surfaces, 60, 62; a transverse wall 64 extending between the parallel intermediate inner walls 56, 58; a threaded outer surface 66; and a cylindrical surface 67 surrounding the groove 44 and a portion of the interior bore 42.

As can be seen in FIG. 21, the spaced inner shoulders 52, 54 of the first spacer segment 32 lie in a plane perpendicular to the central longitudinal axis 68 of the first spacer segment 32, and the spaced intermediate inner walls 56, 58 are spaced from and parallel to the central longitudinal axis 68 of the first spacer segment 32. The intermediate inner walls 56, 58 are adjacent to the inner shoulders 52, 54 and to the transverse wall 64; together, these walls 56, 58, 64 and shoulders 52, 54 define a T-shaped female transverse slot 69. The transverse slot 69 is open at both ends so that the transverse slot is capable of receiving a complementary male portion of the second spacer segment 34 when the first and second spacer segments 32, 34 are assembled as shown in FIGS. 4–6.

Figure 11:
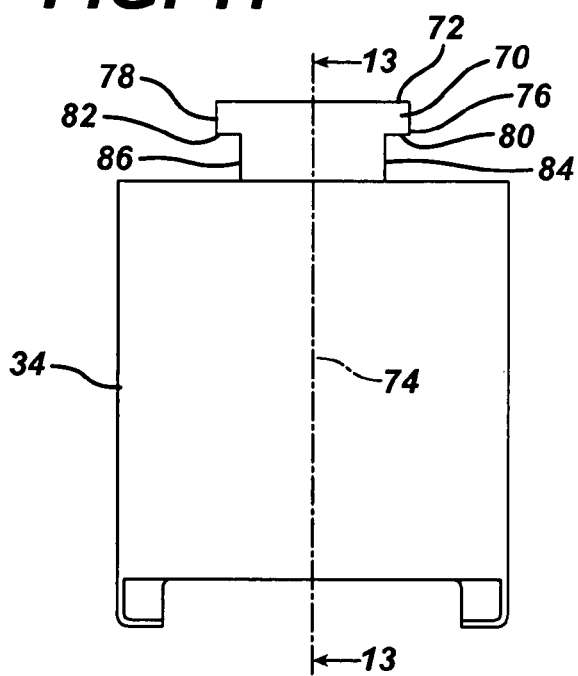
FIG. 11 is a side view or elevation of an embodiment of a second spacer segment for use with the intercalary prosthetic system of the present invention.
Figure 12:
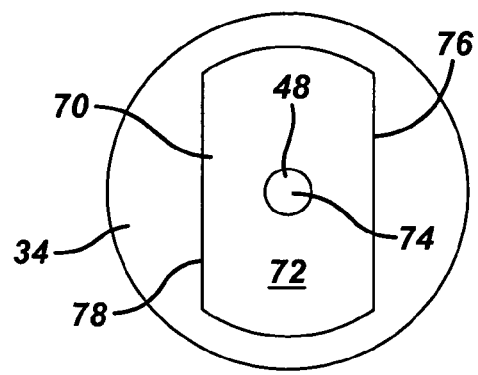
FIG. 12 is a top plan view of the spacer segment of FIG. 11.

A second spacer segment 34 with a male portion 70 complementary to the female portion 50 is illustrated in FIGS. 11–13. The illustrated male portion 70 comprises a transverse projection with a size and shape that complements the size and shape of the transverse slot 69, including the undercuts. As best seen in FIG. 21, the illustrated transverse male portion or projection 70 includes: a transverse end wall 72 perpendicular to the central longitudinal axis 74 of the second trial segment 34; a pair of spaced walls 76, 78 perpendicular and adjacent to the transverse end wall 72; a pair of spaced co-planar shoulders 80, 82 spaced from an parallel to the transverse end wall 72; a pair of spaced parallel intermediate walls 84, 86 perpendicular and adjacent to the shoulders 80, 82; together, walls 76, 78, 84, 86 and shoulders 80, 82 define a T-shaped male projection 70.

The transverse male portion or projection 70 and female transverse slot 69 are sized and shaped so that the first and second spacer segments 32, 34 can be connected together by sliding the transverse male portion or projection 70 into the female transverse slot 69 as shown in FIGS. 4–5. As there shown, the two spacer segments 32, 34 can be connected without moving the spacer segments 32, 34 and bone portions 12, 14 in a proximal-distal direction (that is, without moving the spacer segments 32, 34 along their longitudinal axes 68, 74). Instead, the first and second spacer segments 32, 34 can be connected by moving one or both of the spacer segments 32, 34 in a direction other than the proximal-distal direction, such as in a generally medial-lateral direction as shown in FIG. 4 or in an anterior-posterior direction. By so connecting the two intercalary spacer segments 32, 34, a mid-shaft prosthetic trial or implant can be assembled intraoperatively after the stem components 20, 22 have been inserted or implanted without substantial distraction of the native bone portions 12, 14.

When the male and female portions 70, 69 of the two spacer segments 32, 34 have been slid together in a medial-lateral or anterior-posterior direction into their mating relationship, the ends of the male portion or projection 70 do not extend outward beyond the threads of the threaded outer surface 66 of the first spacer segment 32. To secure the first and second intercalary spacer segments 32, 34 together, the illustrated embodiment of the invention also includes the retaining ring 36 shown in FIGS. 4–6 and 14–21.

Figure 14:
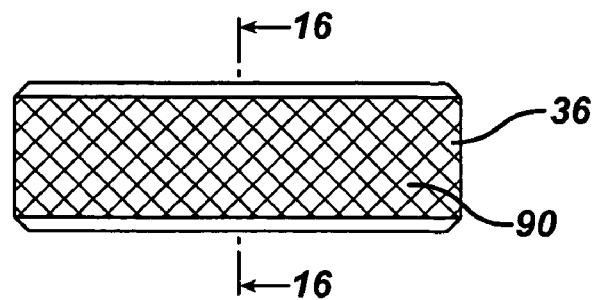
FIG. 14 is a side view or elevation of an embodiment of a retaining ring for use with intercalary prosthetic system of the present invention.
Figure 15:
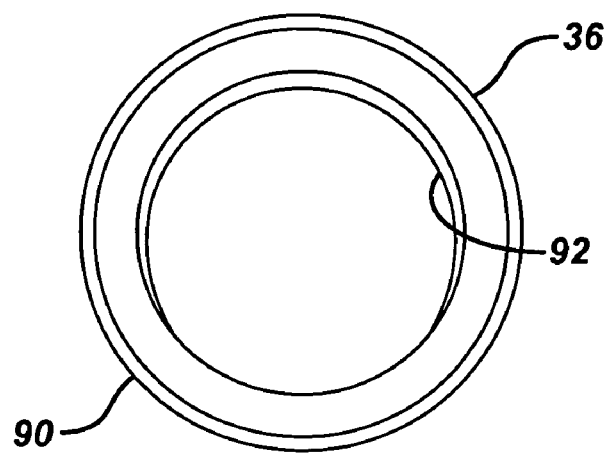
FIG. 15 is a top plan view of the retaining ring of FIG. 14.
Figure 16:
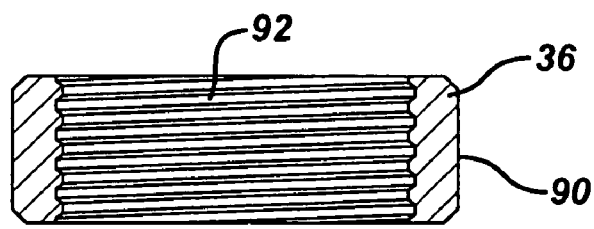
FIG. 16 is a cross-section of the retaining ring of FIGS. 14–15, taken along line 16—16 of FIG. 14.
Figure 17:
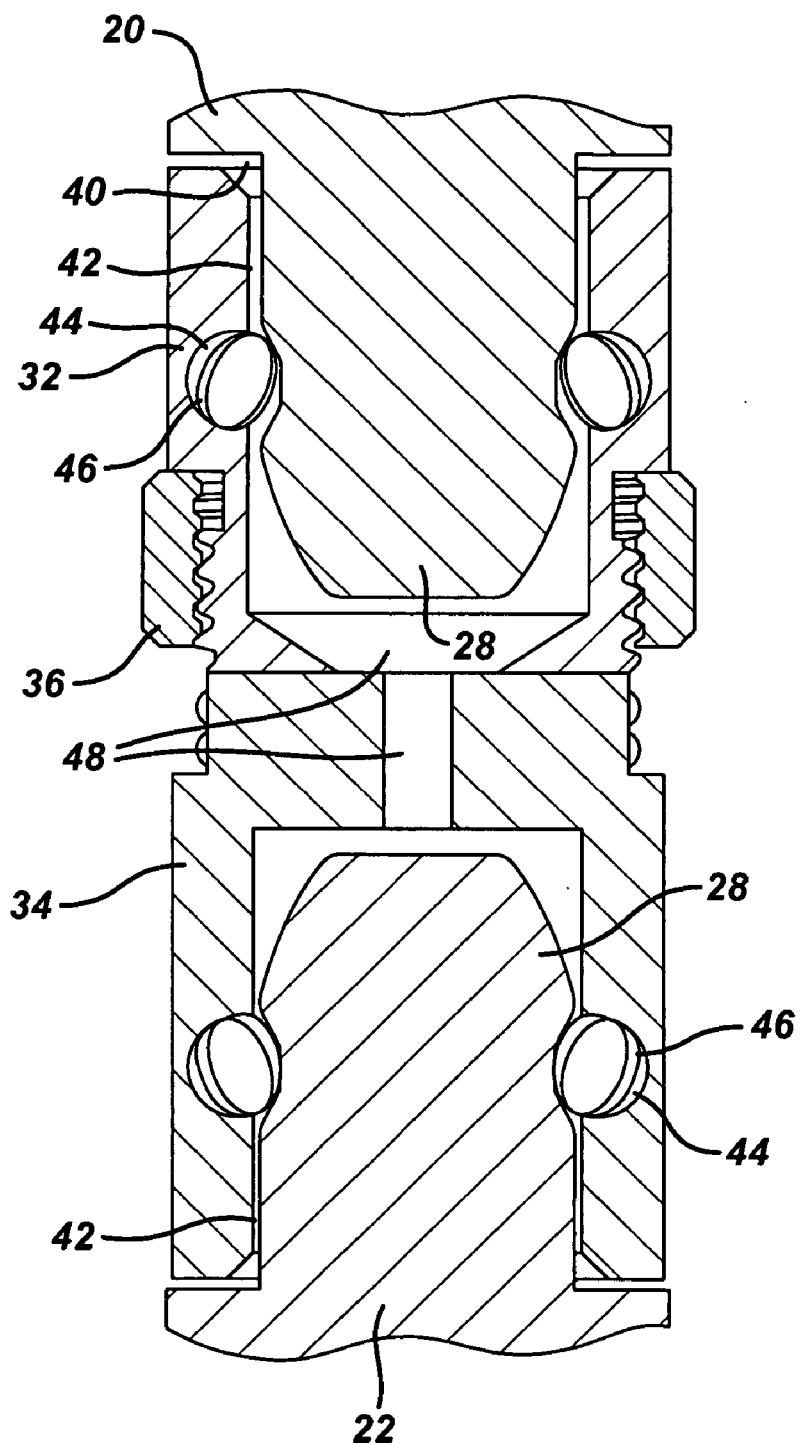
FIG. 17 is a cross-section of the first and second spacer segments assembled with stem components with the retaining ring in the unlocked position, the cross-section being taken along a coronal plane through the assembly illustrated in FIG. 5.
Figure 18:
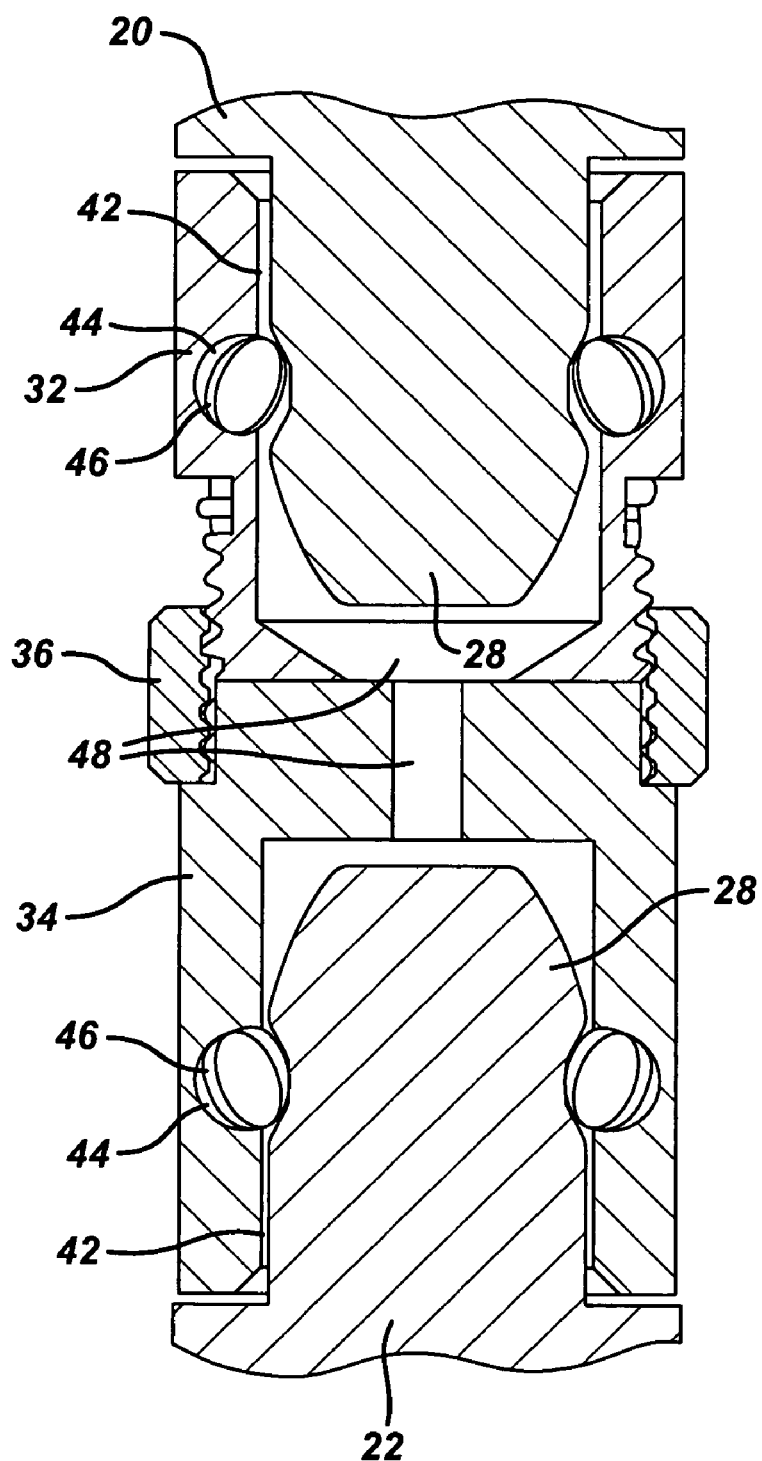
FIG. 18 is a cross-section of the first and second spacer segments assembled with stem components with the retaining ring in the locked position, the cross-section being taken along a coronal plane through the assembly illustrated in FIG. 6.
Figure 19:
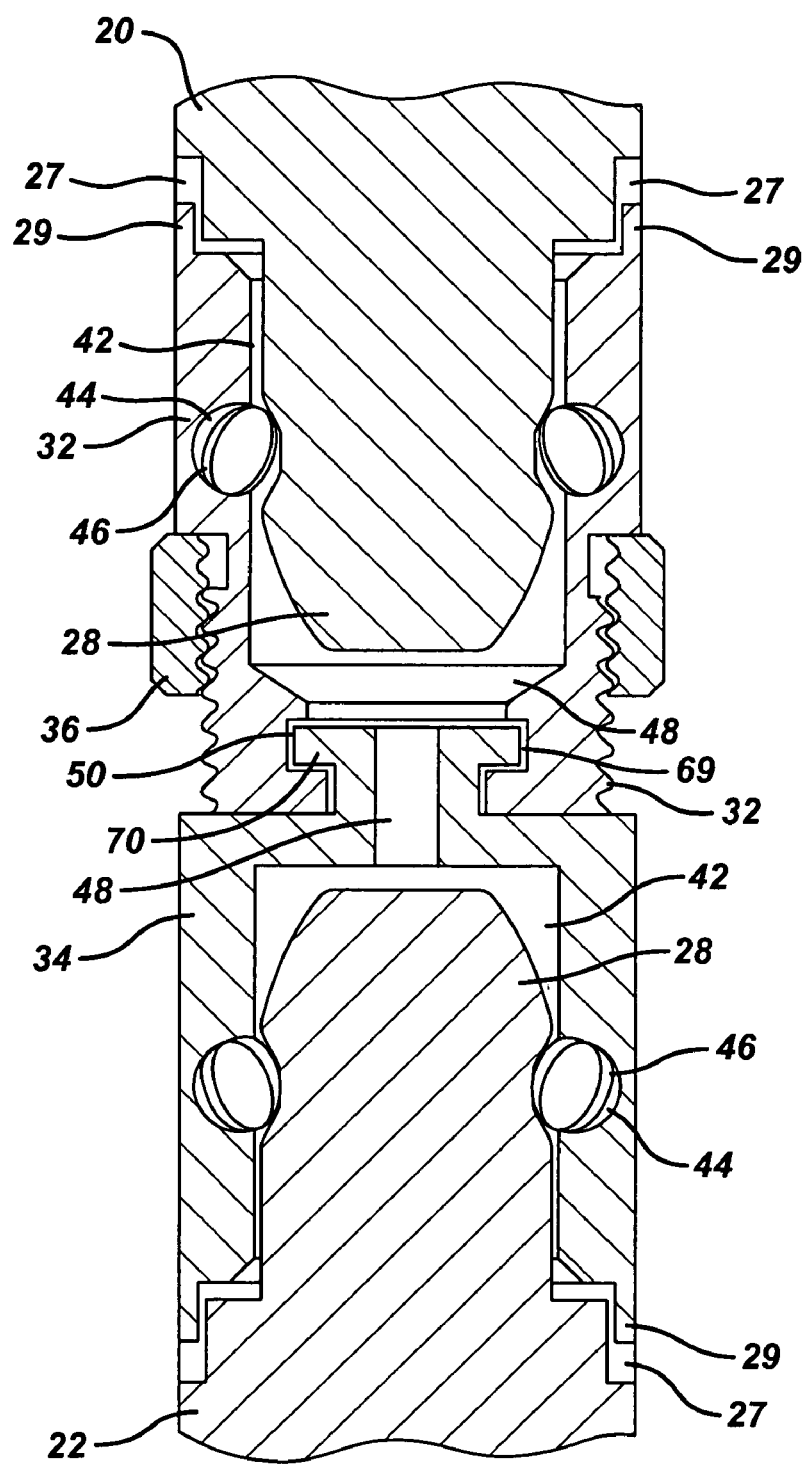
FIG. 19 is a cross-section of the first and second spacer segments assembled with stem components with the retaining ring in the unlocked position, the cross-section being taken along a sagittal plane through line 19—19 of FIG. 5.
Figure 20:
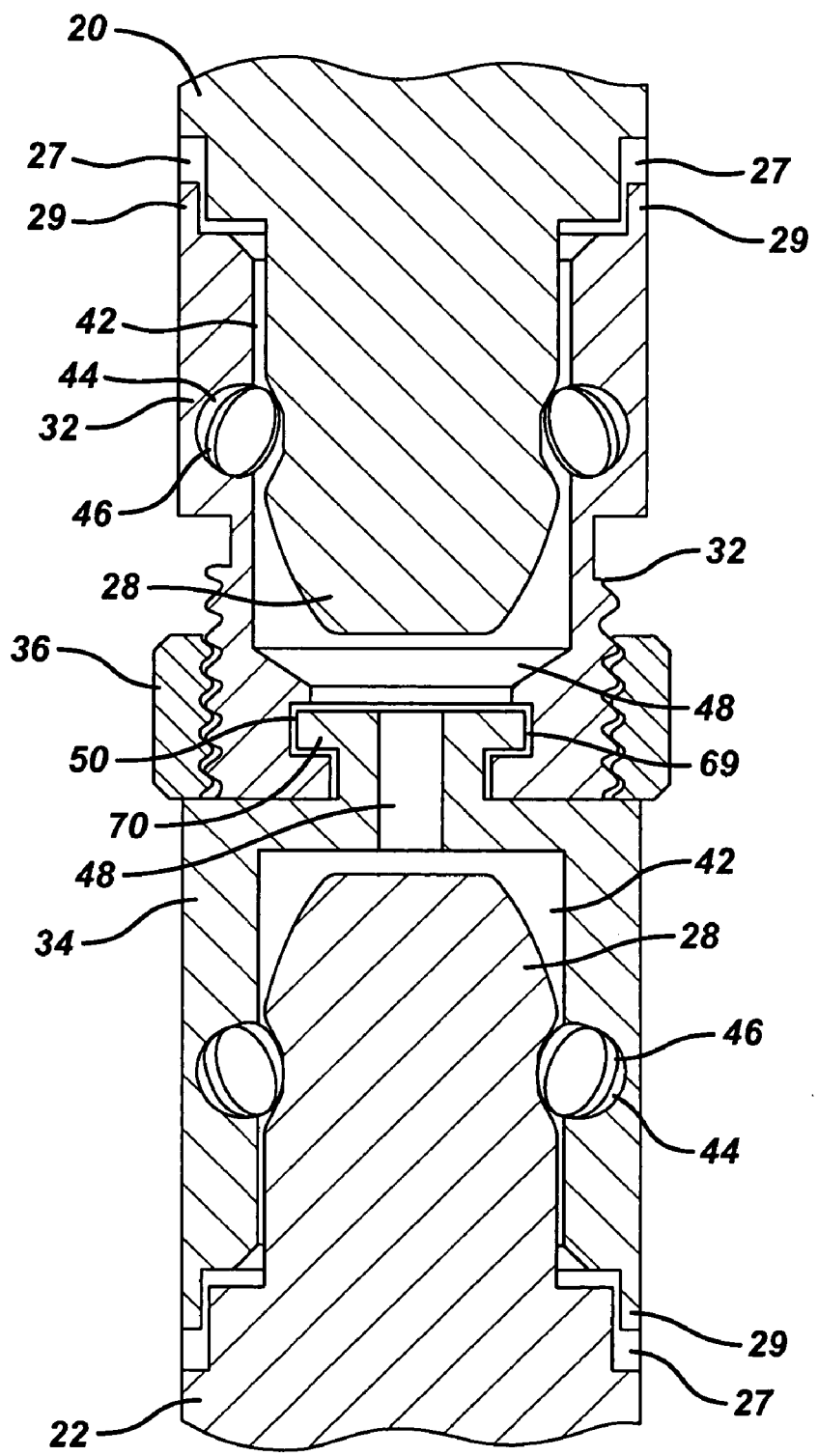
FIG. 20 is a cross-section of the first and second spacer segments assembled with stem components with the retaining ring in the locked position, the cross-section being taken along a sagittal plane through line 20—20 of FIG. 6.

As shown in FIGS. 14–16, the retaining ring 36 is annular, with an outer surface 90 that is knurled or textured in the illustrated embodiment to facilitate turning of the ring by hand during surgery. The interior surface 92 of the retaining ring 36 is threaded, as shown in FIGS. 16 and 21. The interior dimension of the retaining ring 36 and its thread pattern allow the retaining ring to be threaded onto the threaded outer surface 66 of the first spacer segment 32 and moved between an unlocked position and a locked position.

The unlocked position of the retaining ring 36 on the first spacer segment 32 is illustrated in FIGS. 4–5, 17 and 19. In this initial position, the entire transverse female slot 69 of the first spacer segment 32 is exposed, and the male portion 70 of the second spacer segment 34 can be slid into and out of the female slot 69 without interference from the retaining ring 36.

The locked position of the retaining ring 36 on the first spacer segment 32 is illustrated in FIGS. 6, 18 and 20–21. In this locked position, the entire transverse female slot 69 of the first spacer segment 32 is covered by the retaining ring, so that the male portion 70 of the second spacer segment 34 cannot be moved with respect to the slot 69. Thus, when the male portion 70 is received in the slot 69 and the retaining ring 36 is in the locked position, the first and second spacer segments 32, 34 are retained together. To disengage the first and second spacer segments 32, 34, the retaining ring 36 can be turned to return it to its unlocked position, wherein the male portion 70 of the second spacer segment 34 is again free to be slid into and out of the transverse slot 69 of the first spacer segment 32. All engagements and disengagements of the first and second spacer segments 32, 34 can be accomplished without moving the spacer segments 32, 34 in the proximal-distal direction, thus minimizing potential damage to native soft tissue at the native ends 12, 14 of the bone 10.

It should be understood that the lengths of intercalary bone segments 16 needing replacement will vary substantially, depending on many factors, such as the extent of disease or injury or the age or size of the patient. Accordingly, an intercalary system or kit will desirably include first and second spacer segments 32, 34 that yield a variety of combined lengths. For maximum versatility with minimal costs, a surgical kit or trial system utilizing the teachings of the present invention could include the first spacer segment 32 of one length along with a plurality of second spacer segments 34 of various lengths to accommodate the need for different spans of bone loss and different lengths of bone. Alternatively, multiple lengths of either one or both of the spacer segments 50, 32 or 34 could be included in a surgical kit.

The three-part spacer and other components can be made of any standard medical grade material for implants and trials. For example, the spacer segments 32, 34, 36, retaining ring 36 and stem components 20, 22 for use as trials could all be made of a wrought cobalt chrome ccm+ alloy (co-cr-mo MS-100002-1083) or surgical grade stainless steel. For use as implants, these components 32, 34, 36 could be made of titanium or a co-cr-mo alloy, for example.

Figure 24:
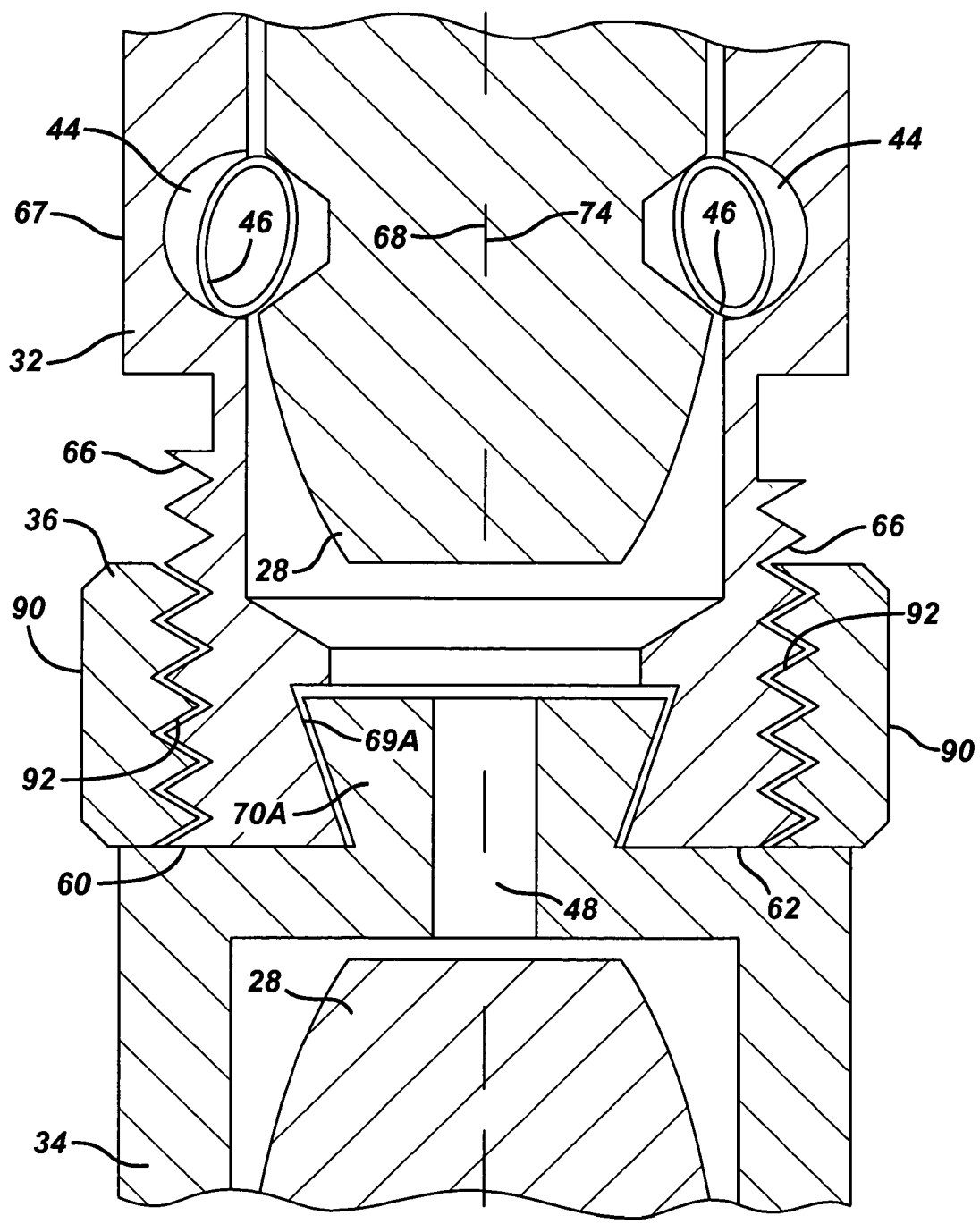
FIG. 24 is an enlarged cross-section of the connection between another embodiment of first and second spacer segments with the retaining ring in the locked position, the male portion and female portion comprising mating dovetail and dovetail slot.
Figure 25:
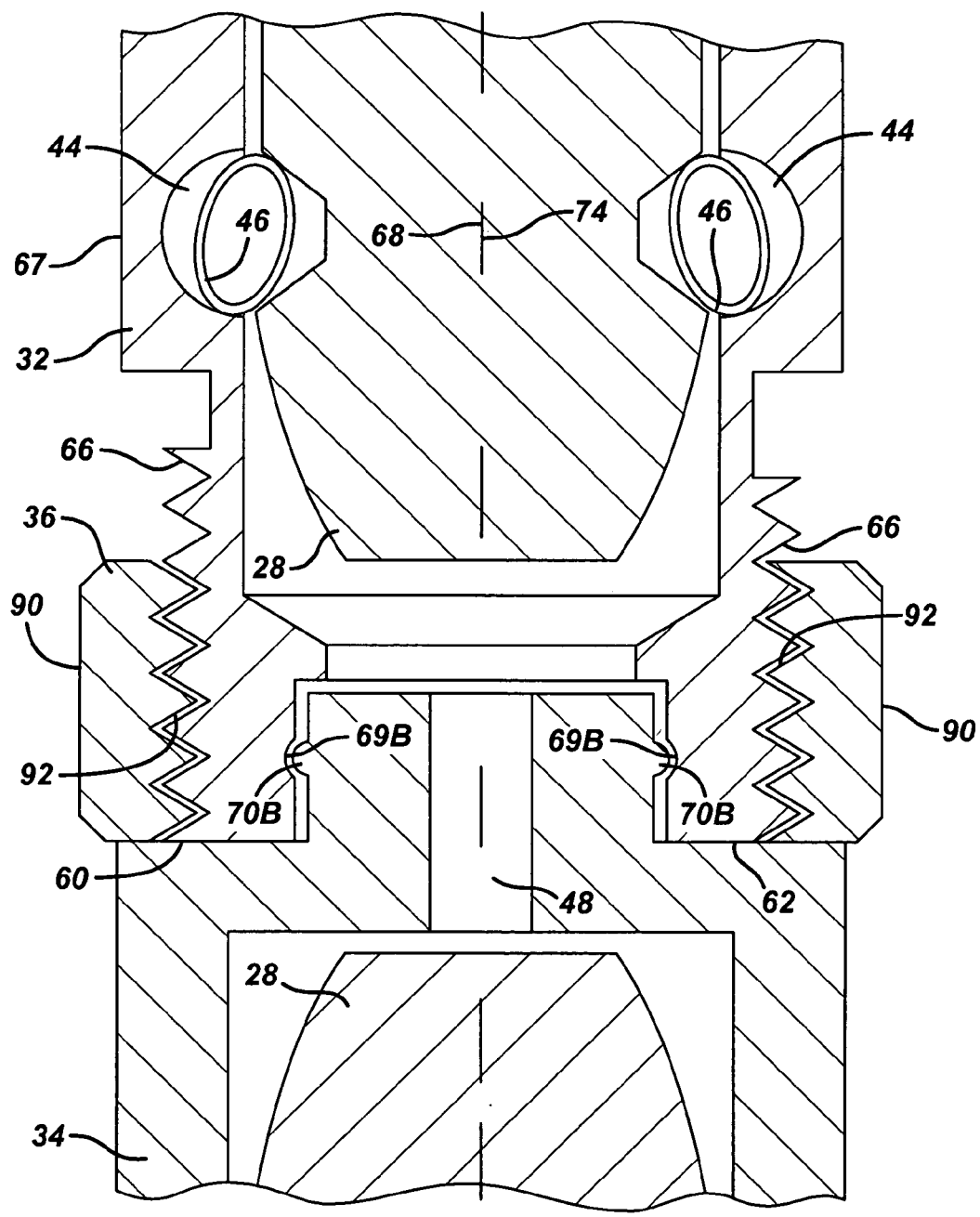
FIG. 25 is an enlarged cross-section of the connection between another embodiment of first and second spacer segments with the retaining ring in the locked position, the male portion and female portion comprising mating tongues and grooves.

It should also be understood that the illustrated mating T-shaped male portion 70 and T-shaped female slot 69 represent one example of an interface that can be used in the present invention, and that other interfaces could be used. For example, as shown in FIG. 24, the male portion 70 and female portion 69 can comprise a mating dovetail 70A and dovetail slot 69A, or as shown in FIG. 25, a tongue 70B and groove 69B configuration could be used. Accordingly, unless expressly limited by the claims to a particular configuration, the "male portion" and "female portion" could comprise any mating projection and opening. Preferably, the mating projection and opening allow the two components to be joined through relative sliding movement (in the medial-lateral direction) rather than through longitudinal movement (in the proximal-distal direction). Similarly, any structure that can selectively limit this relative movement between these two components to lock the components together can serve as a retaining device (such as retaining ring 36).

To use the illustrated intercalary spacer segments 32, 34 and system, the surgeon can prepare the long bone (e.g. the femur, tibia, humerus, etc.) to remove the diseased portion of the diaphyses or to remove bone fragments produced by some injury. The surgeon can then ream the intramedullary canals of the healthy proximal and distal bone portions 12, 14 in a standard manner to receive the stems of the stem trials 20, 22. The inner ends 100, 102 (see FIG. 1) of the native bone portions 12, 14 can be resected to provide a generally flat surface against which the stem trials 20, 22 can seat. As discussed above, for trialing, the surgeon can use the stem components described and illustrated in U.S. patent application Ser. No. 10/135,610.

The surgeon can assemble the illustrated stem component 20 with the illustrated first spacer segment 32 by inserting the male post 28 of the stem component 20 into the bore 42 of the first spacer segment 32 until the appropriate temporary lock is created between the two components 20, 32. The temporary lock can be accomplished through use of the illustrated canted-coil spring 46 in combination with the groove 44 in the first trial segment and groove in the male post 28 of the stem trial. The retaining ring 36 can be assembled with the first spacer segment 32 by threading it onto the threaded outer surface 66 of the first spacer segment until the retaining ring is in the unlocked position, creating a first trial sub-assembly, shown at 104 in FIG. 22. The surgeon can then assemble the other stem component 22 with the second spacer segment 34 by inserting the male post 28 of the stem component 22 into the bore 42 of the second spacer segment 34, creating a second trial sub-assembly shown at 106 in FIG. 23. The stem of each trial sub-assembly can then be temporarily inserted in the prepared intramedullary canal of the respective native bone portion 12, 14.

Once both sub-assemblies 104, 106 have been inserted, the two sub-assemblies 104, 106 can be connected as shown in FIGS. 4–6 to create the intercalary trial assembly. The adjacent male portion 70 and female portion 50 of the sub-assemblies 104, 106 can be moved slightly in a generally medial-lateral direction (or anterior-posterior direction) and the male portion 70 can then be inserted into the female transverse slot 69. No proximal-distal distraction is necessary. The sub-assemblies 104, 106 can then be brought together until the male portion 70 is fully received in the female transverse slot 69. The surgeon can then turn the retaining ring 36 until the retaining ring 36 is moved to the locked position, thus retaining the two sub-assemblies together. If the surgeon is dissatisfied with the assembled trial (for example, if the length of the exposed portion does not result in an even limb length for the patient), the surgeon can quickly and easily disassemble the trial by turning the retaining ring 36 until it reaches the unlocked position and then sliding the male portion 70 out of the female transverse slot 69 (again, without requiring excessive movement in the proximal-distal direction). The surgeon can continue with different sizes of trial segments 32, 34 until satisfied that the final prosthetic implant will best suit the needs of the patient. Once satisfied, the surgeon can then separately remove each sub-assembly 104, 106 from the native bone ends 12, 14 and then can permanently implant an intercalary prosthesis corresponding with the trial assembly that yielded the most satisfactory results.

It should be understood that the above-described surgical technique is provided by way of example only, and that the present invention is not limited to that technique unless expressly called for in the claims. Variations are possible; for example, the surgeon could opt to connect the trial segments 32, 34 and the stem trials 20, 22 after the stem trials have been inserted in the native bone portions 12, 14. Moreover, it should be understood that the above-described surgical technique can be modified for use of the three-part spacer in implants, instruments and other types of systems.

As can be appreciated from the above description, the principles of the invention can also be used outside of the orthopaedic and medical fields. In any field where it is desirable to join two components through transverse rather than longitudinal movement, mating male projections and female slots and retainers similar to those illustrated could be used.

While only specific embodiments of the invention have been described and shown, it is apparent that various alternatives and modifications can be made thereto. Those skilled in the art will also recognize that certain additions can be made to the illustrative embodiment. It is, therefore, the intention in the appended claims to cover all such alternatives, modifications and additions as may fall within the true scope of the invention.

We claim:

1. An orthopaedic system comprising a set of implant components sized and shaped to replace a portion of a bone, a set of trial components sized and shaped to replicate at least one feature of the implant components and a set of instruments for use in preparing the bone to receive the implant components, wherein at least one of the sets includes:

a first member having a longitudinal axis;
a second member having a longitudinal axis; and
a retainer;

one of the members having a male portion and the other of the members having surfaces defining a female portion;

the female portion being capable of receiving the male portion to connect the first and second members together;

wherein the female portion and the male portion are sized and shaped so that the male portion can be moved into the female portion through relative movement in a direction other than longitudinal;

wherein the retainer is movable between an unlocked position wherein relative movement between the male portion and female portion is possible and a locked position wherein relative movement between the male portion and female portion is restricted;

wherein the first member comprises a first spacer segment and the second member comprises a second spacer segment;

where in the portion of bone to be replaced comprises an intercalary bone portion between two native ends of the bone and wherein the first member further includes a proximal stem component connected to the first spacer segment and the second member further includes a distal stem component connected to the second spacer segment, the proximal stem component including a stem sized and shaped to be received in the intramedullary canal of one native end of the bone and the distal stem component having a stem sized and shaped to be received in the intramedullary canal of the other native end of the bone;

wherein the female portion is shaped to define a transverse slot;

wherein the male portion comprises a transverse projection having a size and shape that complements the size and shape of the transverse slot of the female portion; and wherein the transverse projection comprises a pair of spaced parallel shoulders and a pair of spaced parallel intermediate walls adjacent to the spaced parallel shoulders, the spaced parallel intermediate walls defining undercuts.

2. The system of claim 1 wherein: the surfaces defining the female transverse slot include a pair of spaced parallel interior shoulders and a pair of spaced parallel intermediate interior walls adjacent to the spaced parallel interior shoulders, the spaced parallel intermediate interior walls defining undercuts; the spaced parallel shoulders of the projection of the male portion are sized and shaped to be received between the spaced parallel intermediate interior walls of the female portion; and the spaced parallel shoulders of the female portion are sized and shaped to be received adjacent to the spaced parallel intermediate walls of the male portion.

3. The system of claim 2 wherein the female portion has a threaded exterior surface at the level of the spaced parallel intermediate interior walls of the female portion.

4. The system of claim 1 wherein the transverse slot is T-shaped in cross-section and the male portion is T-shaped in cross-section.

5. The system of claim 1 wherein the transverse slot is dovetailed in shape and the male portion is dovetailed in shape.

6. The system of claim 1 wherein the transverse slot includes a groove and the male portion includes a rib.

7. The system of claim 1 wherein the first member and second member comprise intercalary trials.

8. An intercalary orthopaedic system to span a space in the shaft of a long bone between native proximal and distal ends of the long bone, the system comprising:

a first spacer segment to be secured to the native proximal end of the long bone, the first spacer segment having a longitudinal axis;

a second spacer segment to be secured to the native distal end of the long bone, the second spacer segment having a longitudinal axis; and a retaining ring;

one of the spacer segments having a male portion and the other of the spacer segments having surfaces defining a female portion;

the female portion being capable of receiving the male portion to connect the first and second spacer segments together to span the space in the shaft of the long bone;

the female portion having a threaded exterior surface;

wherein the female portion and the male portion are sized and shaped so that the male portion can be moved into the female portion through relative movement in a direction other than longitudinal; and wherein the retaining ring has a threaded interior surface sized and shaped to be capable of being threaded onto the threaded exterior surface of the female portion to retain the first and second spacer segment together when the male portion is received in the female portion.

9. The intercalary orthopaedic system of claim 8 further comprising a proximal stem component connected to the first spacer segment and a distal stem component connected to the second spacer segment, the proximal stem component including a stem sized and shaped to be received in the intramedullary canal of one bone portion and the distal stem component having a stem sized and shaped to be received in the intramedullary canal of the other bone portion.

10. The intercalary orthopaedic system of claim 8 wherein the female portion is shaped to define a transverse slot.

11. The intercalary orthopaedic system of claim 10 wherein the male portion comprises a transverse projection having a size and shape that complements the size and shape of the transverse slot of the female portion.

12. The intercalary orthopaedic system of claim 11 wherein the transverse projection comprises a pair of spaced parallel shoulders and a pair of spaced parallel intermediate walls adjacent to the spaced parallel shoulders, the spaced parallel intermediate walls defining undercuts.

13. The intercalary orthopaedic system of claim 12 wherein: the surfaces defining the female transverse slot include a pair of spaced parallel interior shoulders and a pair of spaced parallel intermediate interior walls adjacent to the spaced parallel interior shoulders, the spaced parallel intermediate interior walls defining undercuts; the spaced parallel shoulders of the projection of the male portion are sized and shaped to be received between the spaced parallel intermediate interior walls of the female portion; and the spaced parallel shoulders of the female portion are sized and shaped to be received adjacent to the spaced parallel intermediate walls of the male portion.

14. The intercalary orthopaedic system of claim 13 wherein the female portion has a threaded exterior wall surface at the level of the spaced parallel intermediate interior walls of the female portion.

15. The intercalary orthopaedic system of claim 10 wherein the transverse slot is T-shaped in cross-section and the male portion is T-shaped in cross-section.

16. The intercalary orthopaedic system of claim 10 wherein the transverse slot is dovetailed in shape and the male portion is dovetailed in shape.

17. The intercalary orthopaedic system of claim 10 wherein the transverse slot includes a groove and the male portion includes a rib.

18. The intercalary orthopaedic system of claim 8 wherein the first spacer segment and second spacer segment comprise trials.

* * * * *